US009084626B1

(12) United States Patent
Asfora

(10) Patent No.: US 9,084,626 B1
(45) Date of Patent: Jul. 21, 2015

(54) SCISSORS SYSTEM FOR SURGICAL CRANIOSYNOSTOSIS TREATMENT

(76) Inventor: Wilson T. Asfora, Sioux Falls, SD (US)

( * ) Notice: Subject to any disclaimer, the term of this patent is extended or adjusted under 35 U.S.C. 154(b) by 1745 days.

(21) Appl. No.: 12/221,620

(22) Filed: Aug. 5, 2008

(51) Int. Cl.
| | |
|---|---|
| *A61B 17/3201* | (2006.01) |
| *A61B 17/32* | (2006.01) |
| *A61B 17/16* | (2006.01) |
| *A61B 18/14* | (2006.01) |
| *A61B 19/00* | (2006.01) |
| *A61B 17/34* | (2006.01) |
| *A61B 18/00* | (2006.01) |

(52) U.S. Cl.
CPC ............ *A61B 17/3201* (2013.01); *A61B 17/16* (2013.01); *A61B 17/32* (2013.01); *A61B 17/3494* (2013.01); *A61B 2018/00595* (2013.01); *A61B 2018/146* (2013.01); *A61B 2018/1452* (2013.01); *A61B 2019/4805* (2013.01)

(58) Field of Classification Search
CPC .................... A61B 2017/1225; A61B 17/3201
See application file for complete search history.

(56) References Cited

U.S. PATENT DOCUMENTS

| | | | | |
|---|---|---|---|---|
| 3,877,145 A | * | 4/1975 | Andrews | 30/231 |
| 4,790,070 A | * | 12/1988 | Olson | 30/134 |
| 5,827,281 A | * | 10/1998 | Levin | 606/51 |
| 5,908,420 A | * | 6/1999 | Parins et al. | 606/51 |
| 5,922,002 A | * | 7/1999 | Yoon | 606/170 |
| 5,951,549 A | * | 9/1999 | Richardson et al. | 606/45 |
| 6,206,877 B1 | * | 3/2001 | Kese et al. | 606/48 |
| 6,358,249 B1 | * | 3/2002 | Chen et al. | 606/45 |
| 6,464,701 B1 | * | 10/2002 | Hooven et al. | 606/50 |
| 2005/0004569 A1 | * | 1/2005 | Witt et al. | 606/51 |

* cited by examiner

*Primary Examiner* — Thomas J Sweet
*Assistant Examiner* — Rebecca Preston
(74) *Attorney, Agent, or Firm* — Jeffrey A. Proehl; Woods, Fuller, Shultz & Smith P.C.

(57) ABSTRACT

A skull bone cutting scissors system is disclosed that comprises a scissors assembly including having first and second members each having a handle portion and a blade portion. The first and second members have an inner periphery and an outer periphery, with at least a section of the inner periphery of the blade portion being sharpened. The second member is pivotally connected to the first member. The first member has a conductive section located along a portion of the inner periphery and the second member has a conductive section located along a portion of the inner periphery. The system includes a cautery energizing apparatus in electrical communication with the conductive section of the first member and the conductive section of the second member. The cautery energizing apparatus is configured to provide power to the conductive sections of the first member and the second member.

15 Claims, 3 Drawing Sheets

SCISSORS SYSTEM FOR SURGICAL CRANIOSYNOSTOSIS TREATMENT

BACKGROUND

1. Field

The present disclosure relates to scissors, and more particularly pertains to a new surgical scissors system for performing craniosynostosis remedial surgery.

2. Description of the Prior Art

Craniosynostosis is the premature fusion of the sutures or joints of the bony plates forming the skull of an infant. The craniosynostosis condition is often treated by invasive surgery to separate the fused bones of the skull along the suture lines, and quite often also involves removing a portion or strip of the skull along the prematurely fused suture to restore the spacing that is found in the skull of healthy infants.

However, the procedure for removing the portion of the skull can be difficult due to the need to open the scalp and the proximity of the tool for cutting the skull to the infant's brain. Conventionally, a scissors has been used to cut the bone of the skull that is rather large and bulky, and has been difficult to use in the confined area between the dura mater covering the brain and the scalp of the patient without opening the scalp of the patient, which causes additional trauma the patient, additional healing time, and may cause additional scarring of the scalp where hair will not regrow.

It is therefore believed that there exists in the art a need for a scissors system that is better suited to the surgery involved to ameliorate the craniosynostosis condition and facilitate healing after the surgery.

SUMMARY

In view of the foregoing disadvantages inherent in the known scissors, the present disclosure describes a new scissors system which may be utilized for performing craniosynostosis remedial surgery.

The present disclosure relates to a new skull bone cutting scissors system that includes a scissors assembly comprises a first member having a proximal end and a distal end. The first member has a handle portion located toward the proximal end and a blade portion located toward the distal end. The first member has an inner periphery and an outer periphery, and at least a section of the inner periphery of the blade portion is sharpened. The second member has a proximal end and a distal end. The second member has a handle portion located toward the proximal end and a blade portion located toward the distal end. The second member has an inner periphery and an outer periphery, and at least a section of the inner periphery of the blade portion is sharpened. The second member is pivotally connected to the first member. The first member has a conductive section located along a portion of the inner periphery, and the second member has a conductive section located along a portion of the inner periphery. The system further includes a cautery energizing apparatus in electrical communication with the conductive section of the first member and the conductive section of the second member. The cautery energizing apparatus is configured to provide power to the conductive sections of the first member and the second member.

In another aspect of the disclosure, a skull bone cutting scissors system includes a scissors assembly comprising a first member having a proximal end and a distal end. The first member has a handle portion located toward the proximal end and a blade portion located toward the distal end. The first member has an inner periphery and an outer periphery, and at least a section of the inner periphery of the blade portion is sharpened. The second member has a proximal end and a distal end. The second member has a handle portion located toward the proximal end and a blade portion located toward the distal end. The second member has an inner periphery and an outer periphery, and at least a section of the inner periphery of the blade portion is sharpened. The second member is pivotally connected to the first member. The first member has a flange located along at least a portion of the outer periphery such that a width of the first member at the outer periphery is greater than the width of the first member at the inner periphery.

The foregoing is a general outline of some of the more significant aspects of the disclosure, and the detailed description of this application that follows discloses additional features of the disclosure which form the subject matter of the claims appended hereto.

The advantages of the various embodiments of the present disclosure, along with the various features of novelty that characterize the embodiments, are disclosed in the following descriptive matter and accompanying drawings.

BRIEF DESCRIPTION OF THE DRAWINGS

The disclosure will be better understood when consideration is given to the following detailed description thereof. Such description makes reference to the annexed drawings wherein.

DESCRIPTION OF PREFERRED EMBODIMENTS

Figure 1:
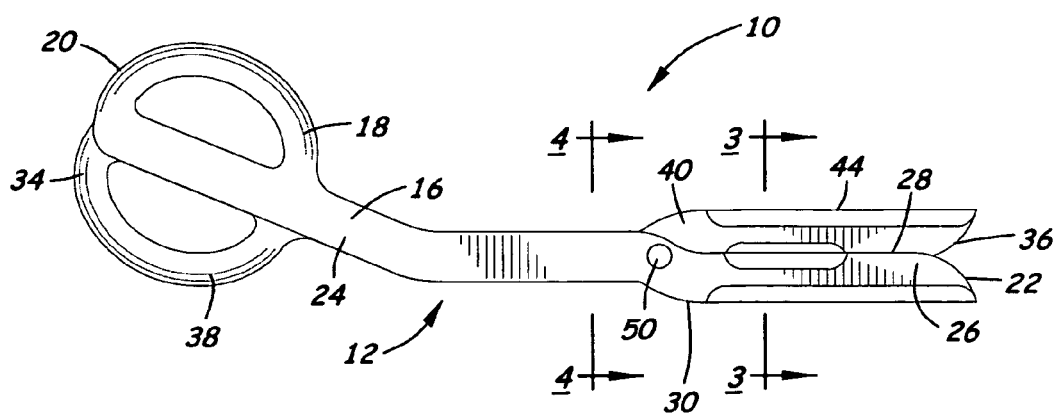
FIG. 1 is a schematic side view of a new surgical scissors according to the present disclosure shown in a closed position.

With reference now to the drawings, and in particular to FIGS. 1 through 5 thereof, the scissors system of the present disclosure is generally designated by the reference numeral 10 in this description.

A skull bone cutting scissors system 10 of this disclosure is highly suitable for use in surgical procedures to remedy or treat craniosynostosis, or the premature fusion of the sutures of the plates forming the skull of an infant. The system may include a scissors assembly 12 for cutting the bone of the skull, and a cautery energizing apparatus 14 for energizing the cautery elements on the scissors assembly.

Figure 2:
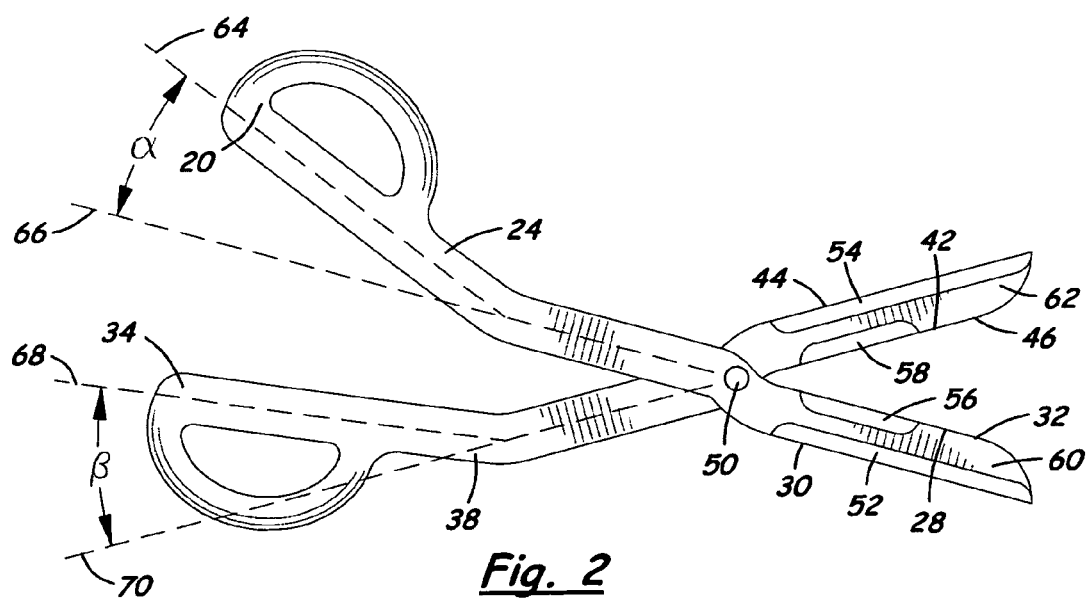
FIG. 2 is a schematic side view of the surgical scissors, according to another illustrative embodiment shown in an open position.

The scissors assembly 12 may include a first member 16 and a second member 18 (see FIGS. 1 and 2). The first member 16 may have a proximal end 20 and a distal end 22, with a handle portion 24 being located toward the proximal end 20 and a blade portion 26 being located toward the distal end 22. The first member 16 may have an inner periphery 28 and an outer periphery 30. At least a section of the inner periphery 28 of the blade portion 26 may have a sharpened edge 32. In some embodiments, the portion of the inner periphery 28 is configured to provide a cutting surface having a length of approximately 1 to approximately 2 cm, and may be approximately 1.5 cm in some embodiments.

Similarly, but not necessarily identically, the second member 18 has a proximal end 34 and a distal end 36, with a handle portion 38 located toward the proximal end 34 and a blade portion 40 located toward the distal end 36. The second member 18 may have an inner periphery 42 and an outer periphery 44. At least a section of the inner periphery 42 of the blade portion has a sharpened edge 46. The second member 18 may be pivotally connected to the first member by a pivot 50. The pivot 50 may comprise a pivot pin that extends from the second member 18 to the first member 16.

In various embodiments of the scissors assembly 12, the width or thickness of the first member 16 at the outer periphery 30 is greater or thicker than the width of the first member at the inner periphery 28. In some embodiments, the first member 16 has a flange 52 located along at least a portion of the outer periphery 30 (see FIGS. 2 and 3). The flange 52 may have a width that is at least approximately twice the width of the first member 16 at the inner periphery 28. The enlarged width, which in some cases is embodied as the flange 52, facilitates the movement of the outer periphery 30 over the dura mater located about the brain of the patient. The enlarged width at the outer periphery 30 makes it less likely that the outer periphery will cut or puncture or otherwise injure the dura when the outer periphery contacts and moves across the dura.

Figure 3:
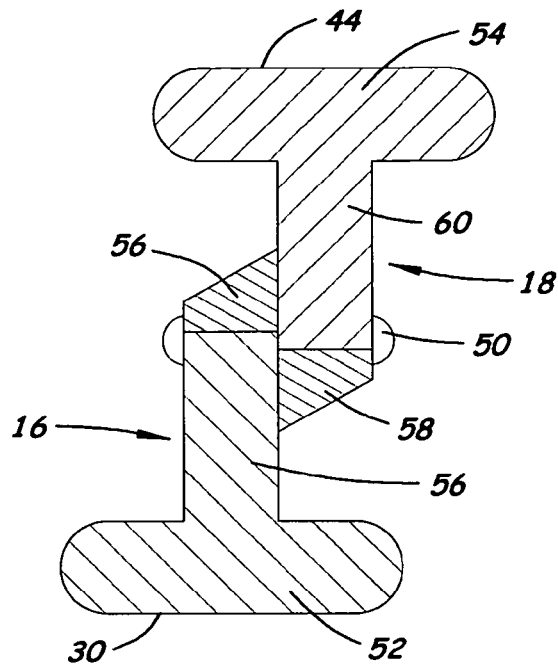
FIG. 3 is a schematic sectional view of the surgical scissors, according to an illustrative embodiment, taken along line 3-3 of FIG. 1.

Similarly, but not necessarily identically, the width or thickness of the second member 18 may be relatively greater or wider or thicker at the outer periphery 44 than the width at the inner periphery 42 (see FIG. 3). In some embodiments, the second member 18 may have a flange 54 located along at least a portion of the outer periphery 44. The flange 52 may have a width that is at least approximately twice the width of the second member 18 at the inner periphery 42, although it is contemplated that the width of the flange 54 on the second member 18 may be relatively narrower than the flange 52 on the first member 16. The enlarged width, such as the flange 54, at the outer periphery 44 decreases the likelihood that the inner surface of the scalp of the patient will be damaged or injured by the outer periphery as the outer periphery contacts and moves along the inner surface.

Significantly, in various embodiments of the system 10 that include a cautery capability, the first member 16 may have a conductive section 56 located along a portion of the inner periphery 28 of the member 16, and the second member 18 has a conductive section 58 located along a portion of the inner periphery 42 of the member 18 (see FIGS. 1 through 3). The conductive sections 56, 58 may be located along portions of the respective sharpened edges 32, 46 of the first 16 and second 18 members, and the portions of the sharpened edges 32, 46 may be located on the respective blade portions 26, 40 toward the pivot 50 and may be located away from the distal ends 22, 36 of the first 16 and second 18 members. As a result, the areas of the skull bone that are most likely to be contacted by the sharpened edges 32, 46 are also most likely to be contacted by the conductive sections 56, 58 of the blade portion 26. The conductive sections 56, 58 may be formed of a conductive material or a material that readily or easily conducts electricity and may also conduct, to some degree, heat.

The first member 16 and the second member 18 may also include a remainder section 60 and a remainder section 62, respectively, and these remainder sections 60, 62 may each be formed of a material that does not conduct, or does not readily conduct, electricity and/or heat. The remainder sections 60, 62 may be located along portions of the sharpened edges 32, 46, and may be located toward the distal ends 22, 36 of the blade portions 26, 40 of the members 16, 18. In this way, the cautery function or effect may be performed by a relatively limited, or at least not along the entire, portion of the sharpened edge 32, 46 of the first 16 and second 18 members. The conductive sections 56, 58 may occupy only about half of the sharpened edge, with the remainder sections 60, 62 occupying the rest. Optionally the percentage occupied by the conductive section may be more or less than the approximately one-half, but it is desirable to minimize the conductive section so that the cautery effect is enhanced.

The scissors assembly 12 may include additional features that enhance the bone cutting ability of the system 10 within a confined space such as is encountered between the brain and dura and the scalp of a patient. As an example, the distance between the pivot 50 and the proximal ends 22, 36 of the first 16 and second 18 members may be more than 1.5 times the distance between the pivot and the distal end of the first member. In some more preferred embodiments, the distance between the pivot 50 and the proximal ends 20, 34 of the members 16, 18 may be between approximately two and approximately three times the distance between the pivot 50 and the distal ends 22, 36. In some embodiments, this relationship may be approximately three to approximately four times. These distance or length relationships enhance the force that may be applied to the skull, especially at areas of the sharpened edges located toward the pivot 50. Significantly, these relationships help to minimize the spread between the distal ends 22, 36 of the members 16, 18 for fitting between the dura and the inner surface of the scalp.

Another optional feature or relationship of the scissors system is the positioning or orientation of at least a section of the handle portions 24, 38 with respect to the respective blade portions 26, 40.

More specifically, the handle portion 24 of the first member 16 has a longitudinal axis 64, and the blade portion 26 of the first member has a longitudinal axis 66, and similarly the handle portion 38 of the second member 38 has a longitudinal axis 68 and the blade portion 40 has a longitudinal axis 70. In some embodiments, the longitudinal axis 64 of the handle portion 24 and the longitudinal axis 66 of the blade portion 26 of the first member 16 form a non-zero angle $\alpha$ with respect to each other, and the longitudinal axis 68 of the handle portion 38 and the longitudinal axis 66 of the blade portion 40 of the second member 18 form a non-zero angle $\beta$ with respect to each other. The angle $\alpha$ and the angle $\beta$ may be similar or the same, or may be different from each other. The angles may range between approximately 0 degrees and approximately 45 degrees, and preferably may be between approximately 10 degrees and approximately 40 degrees.

Figure 4:
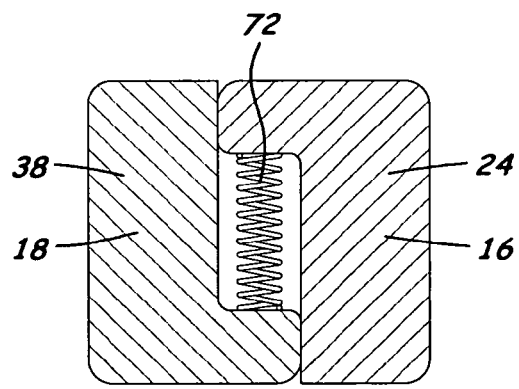
FIG. 4 is a schematic sectional view of the surgical scissors taken along line 4-4 of FIG. 1

Optionally, the first portion 16 and the second portion 18 may be biased into an open position by a biasing member, such as a spring 72, acting on the portions (see FIG. 4).

Figure 6:
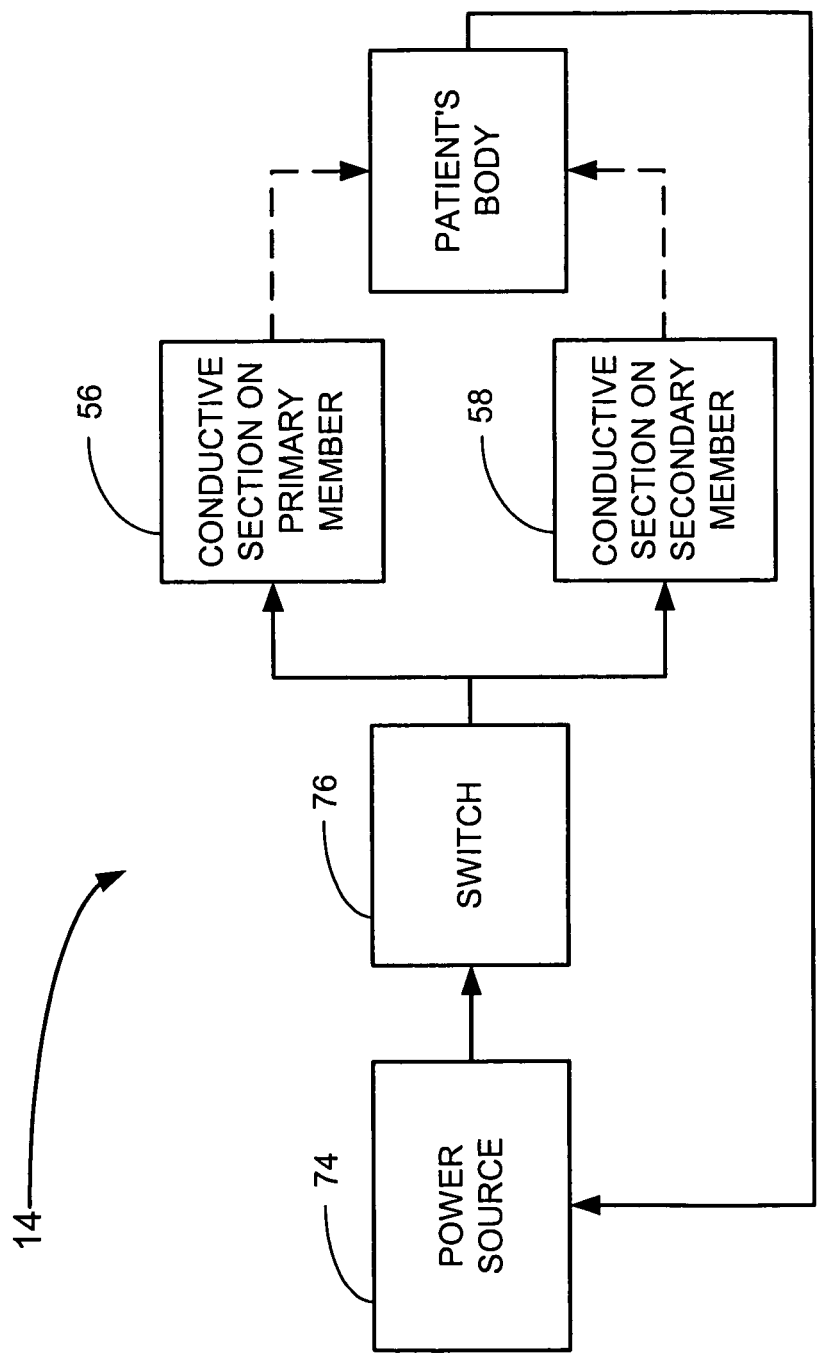
FIG. 6 is a schematic diagram of a system employing the surgical scissors.

The cautery apparatus 14 is provided to energize the conductive sections of the first member and the second member to produce the cauterizing action or effect on the tissue, such the bone of the skull, while being cut by the scissors 12 (SEE FIG. 6). The cautery apparatus 14 that is employed to energize the conductive sections 56, 58 may comprise any known cauterizing technology, and may include a power source 74 and a switch 76 in communication with the power source. The switch 74 may be switched "on" to provide the conductive sections 56, 58 with power to cause cauterization of the tissue, and "off" to stop the supply of power to the sections 56, 58.

Other techniques or apparatus may be employed to energize the conductive sections 56, 58 on the scissors.

Figure 5:
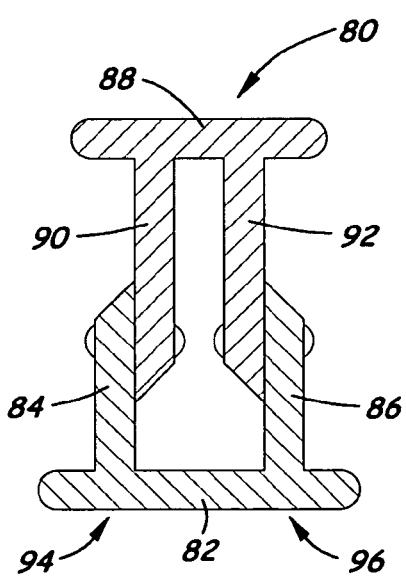
FIG. 5 is schematic sectional view of an optional embodiment of the surgical scissors having a pair of blades portions on each of the first and second members.

Optional embodiments of the system 10, such as is shown in FIG. 5, are highly suitable for forming two cuts simultaneously to remove a strip of bone from the surrounding bone. In one such embodiment 80, a first member 82 comprises a first blade portion 84 and a second blade portion 86. A second member 88 comprises a first blade portion 90 and a second blade portion 92. The first blade portion 84 of the first member 82 and the first blade portion 90 of the second member 88 may be arranged to form a first shear 94 and the second blade portion 86 of the first member 82 and the second blade portion 92 of the second member 88 are arranged to form a second shear 96. The first shear 94 and the second shear 96 may be positioned to form substantially parallel cuts to thereby be able to cut a strip from surrounding bone. This feature of the disclosure permits the reduction in time required to make the cuts, as well as potentially reducing trauma to the surgical area, especially in situations where the strip of bone to be removed is relatively thin.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

In addition, in the foregoing Detailed Description, it can be seen that various features are described in the context of a single embodiment for the purpose of streamlining the disclosure. The disclosure of a single embodiment is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment. In the appended claims, the terms "including" and "in which" are used as the plain-English equivalents of the respective terms "comprising" and "wherein," respectively. Moreover, the terms "first," "second," and "third," etc. are used merely as labels, and are not intended to impose numerical requirements on their objects. Further, where the term "substantially" is used, it is intended to mean "for the most part" or "being largely but not wholly that which is specified".

The foregoing is considered as illustrative only of the principles of the disclosure. Further, since numerous modifications and changes will readily occur to those skilled in the art in view of the disclosure of this application, it is not desired to limit the disclosure to the exact embodiments, implementations, and operations shown and described. Accordingly, all equivalent relationships to those illustrated in the drawings and described in the specification, including all suitable modifications, are intended to be encompassed by the present disclosure that fall within the scope of the disclosure.

I claim:

1. A skull bone cutting scissors system comprising:
a scissors assembly comprising:
a first member having a proximal end and a distal end, the first member having a handle portion located toward the proximal end and a blade portion located toward the distal end, the first member having an inner periphery and an outer periphery, at least a section of the inner periphery of the blade portion forming a first cutting edge;
a second member having a proximal end and a distal end, the second member having a handle portion located toward the proximal end and a blade portion located toward the distal end, the second member having an inner periphery and an outer periphery, at least a section of the inner periphery of the blade portion forming a second cutting edge;
wherein the second member is pivotally connected to the first member to move the first cutting edge of the first member along the second cutting edge of the second member to shear bone material contacted by the converging cutting edges of the first and second members;
wherein the first member has a conductive section located along a portion of the first cutting edge on the inner periphery of the first member;
wherein the second member has a conductive section located along a portion of the second cutting edge of the inner periphery of the second member; and
a cautery energizing apparatus in electrical communication with the conductive section on the first cutting edge of the first member and the conductive section on the second cutting edge of the second member, the cautery energizing apparatus being configured to provide power to the conductive sections of the first member and the second member;
wherein each of the blade portions of the first and second members has a pair of opposite faces;
a first flange located along at least a portion of the outer periphery of the first member and extending outwardly from at least one of the opposite faces of the blade portion, and a second flange located along at least a portion of the outer periphery of the second member and extending outwardly from at least one of the opposite faces of the blade portion; and
wherein the conductive sections of the first and second cutting edges are entirely located in a space between the first and second flanges;
wherein the handle portion of the first member has a longitudinal axis and the blade portion of the first member has a longitudinal axis, the longitudinal axis of the handle portion and the longitudinal axis of the blade portion forming a non-zero angle.

2. The skull bone cutting scissors system of claim 1 wherein the first member has a remainder section that is non-conductive and the second member has a remainder section that is non-conductive.

3. The skull bone cutting scissors system of claim 1 wherein the first member and the second member each have a width, the width of the flange of each member being at least twice the width along the cutting edge at the inner periphery.

4. The skull bone cutting scissors system of claim 1 wherein the flange on each of the first and second members extends perpendicularly outwardly from both of the opposite faces of the blade portion of the respective member such that the space extends beyond the opposite faces of the blade portions.

5. The skull bone cutting scissors system of claim 1 wherein the flange on each of the first and second members has a width being approximately three times the width of the first and second members at the outer periphery of each member.

6. The skull bone cutting scissors system of claim 1 wherein the second member is connected to the first member by a pivot, and a distance between the pivot and the proximal end of the first member being at least approximately 1.5 times a distance between the pivot and the distal end of the first member.

7. A skull bone cutting scissors system comprising:
   a scissors assembly comprising:
      a first member having a proximal end and a distal end, the first member having a handle portion located toward the proximal end and a blade portion located toward the distal end, the first member having an inner periphery and an outer periphery, at least a section of the inner periphery of the blade portion forming a first cutting edge;
      a second member having a proximal end and a distal end, the second member having a handle portion located toward the proximal end and a blade portion located toward the distal end, the second member having an inner periphery and an outer periphery, at least a section of the inner periphery of the blade portion forming a second cutting edge;
      wherein the second member is pivotally connected to the first member to move the first cutting edge of the first member along the second cutting edge of the second member to shear bone material contacted by the converging cutting edges of the first and second members;
      wherein the first member has a conductive section located along a portion of the first cutting edge on the inner periphery of the first member;
      wherein the second member has a conductive section located along a portion of the second cutting edge of the inner periphery of the second member; and
   a cautery energizing apparatus in electrical communication with the conductive section on the first cutting edge of the first member and the conductive section on the second cutting edge of the second member, the cautery energizing apparatus being configured to provide power to the conductive sections of the first member and the second member;
   a first flange located along at least a portion of the outer periphery of the first member and a second flange located along at least a portion of the outer periphery of the second member, the conductive sections of the first and second cutting edges being entirely located in a space between the first and second flanges;
   wherein the first member has a remainder section that is non-conductive and the second member has a remainder section that is non-conductive;
   wherein the first member has a width, the width of the first member at the outer periphery being greater than the width at the inner periphery;
   wherein the first flange has a width being at least twice the width of the first member at the outer periphery;
   wherein the second member has a width, the width of the second member at the outer periphery being greater than the width at the inner periphery;
   wherein the second flange has a width being at least twice the width of the second member at the outer periphery;
   wherein the second member is connected to the first member by a pivot, and a distance between the pivot and the proximal end of the first member being at least approximately 1.5 times a distance between the pivot and the distal end of the first member;
   wherein the handle portion of the first member has a longitudinal axis and the blade portion of the first member has a longitudinal axis, the longitudinal axis of the handle portion and the longitudinal axis of the blade portion forming a non-zero angle; and
   wherein the non-zero angle is between approximately 1 degree and 45 degrees, inclusive.

8. A skull bone cutting scissors system comprising:
   a scissors assembly comprising:
      a first member having a proximal end and a distal end, the first member having a handle portion located toward the proximal end, a first blade portion located toward the distal end, and a second blade portion located toward the distal end, the first and second blade portions of the first member each having an inner periphery and an outer periphery, at least a section of the inner periphery of the first blade portion forming a first cutting edge, at least a section of the inner periphery of the second blade portion forming a second cutting edge;
      a second member having a proximal end and a distal end, the second member having a handle portion located toward the proximal end, a first blade portion located toward the distal end, and a second blade portion located toward the distal end, the first and second blade portions of the second member each having an inner periphery and an outer periphery, at least a section of the inner periphery of the first blade portion forming a first cutting edge, at least a section of the inner periphery of the second blade portion forming a second cutting edge;
      wherein the second member is pivotally connected to the first member to move the first cutting edge of the first member along the first cutting edge of the second member to form a first shear and move the second cutting edge of the first member along the second cutting edge of the second member to form a second shear to shear bone material contacted by the converging cutting edges of the first and second shears;
      wherein the first member has a conductive section located along a portion of the inner periphery of the first cutting edge and along a portion of the inner periphery of the second cutting edge of the first member;
      wherein the second member has a conductive section located along a portion of the inner periphery of the first cutting edge and along a portion of the inner periphery of the second cutting edge of the second member; and
      wherein the first shear and the second shear are positioned to form substantially parallel cuts to cut a strip from surrounding bone; and
   a cautery energizing apparatus in electrical communication with the conductive section on the first cutting edge and the second cutting edge of the first member and the conductive section on the first cutting edge and the second cutting edge of the second member, the cautery energizing apparatus being configured to provide power to the conductive sections of the first member and the second member.

9. The skull bone cutting scissors system of claim 8 wherein the first member has a first flange located along at least a portion of the outer peripheries and the second member has a second flange located along at least a portion of the outer peripheries with the conductive sections of the first and second cutting edges being located in a space between the first and second flanges.

10. The skull bone cutting scissors system of claim 9 wherein the first flange extends between the first blade portion and the second blade portion of the first member, and wherein the second flange extends between the first blade portion and the second blade portion of the second member.

11. The skull bone cutting scissors system of claim 9 wherein each of the first and second blade portions of the first and second members has a pair of opposite faces, and the flange on each of the first and second members extends perpendicularly outwardly from both of the opposite faces of the first and second blade portions of the respective member such that the space extends beyond the opposite faces of the blade portions.

12. The skull bone cutting scissors system of claim 11 wherein the first member and the second member each have a width, the width of the flange at the outer periphery of each member being at least twice the width along the first cutting edge at the inner periphery.

13. The skull bone cutting scissors system of claim 8 wherein the second member is connected to the first member by a pivot, and a distance between the pivot and the proximal end of the first member being at least approximately 1.5 times a distance between the pivot and the distal end of the first member.

14. The skull bone cutting scissors system of claim 8 wherein the handle portion of the first member has a longitudinal axis and the blade portion of the first member has a longitudinal axis, the longitudinal axis of the handle portion and the longitudinal axis of the blade portion forming a non-zero angle.

15. The skull bone cutting scissors system of claim 8 wherein the first member has a remainder section that is non-conductive and the second member has a remainder section that is non-conductive.

* * * * *